US00PP26409P2

(12) United States Plant Patent
Skotak, Jr.

(10) Patent No.: US PP26,409 P2
(45) Date of Patent: Feb. 9, 2016

(54) ***TILLANDSIA* HYBRID PLANT NAMED 'DURAANT'**

(50) Latin Name: ***Tillandsia* hybrid.**
Varietal Denomination: Duraant

(71) Applicant: Chester Skotak, Jr., Alajuela (CR)

(72) Inventor: Chester Skotak, Jr., Alajuela (CR)

( * ) Notice: Subject to any disclaimer, the term of this patent is extended or adjusted under 35 U.S.C. 154(b) by 0 days.

(21) Appl. No.: 14/544,001

(22) Filed: Nov. 12, 2014

(51) Int. Cl.
*A01H 5/02* (2006.01)

(52) U.S. Cl.
USPC ..... Plt./370

(58) Field of Classification Search
USPC ..... Plt./263.1, 370
See application file for complete search history.

*Primary Examiner* — Susan McCormick Ewoldt
*Assistant Examiner* — Karen Redden
(74) *Attorney, Agent, or Firm* — Samuel R. McCoy, Jr.

(57) ABSTRACT

'Duraant' is a distinctive variety of *Tillandsia* hybrid which is characterized by the combination of dark green foliage, striking pink bracts and highly branched inflorescences, as well as the stability and uniformity of traits through successive cycles of asexual propagation.

2 Drawing Sheets

Latin name of the genus and species: The Latin name of the genus and species of the novel variety disclosed herein is *Tillandsia* hybrid.

Variety denomination: The inventive variety of *Tillandsia* hybrid disclosed herein has been given the variety denomination 'Duraant'.

BACKGROUND OF THE INVENTION

The present invention relates to a new and distinct cultivar of *Tillandsia* hybrid, which has been given the variety denomination of 'Duraant'. Its market class is PLT/370.

Parentage: The *Tillandsia* hybrid variety 'Duraant' is the result of a controlled pollination breeding program carried out in April of 2006 in Alajuela, Costa Rica. 'Duraant' is a progeny of said breeding program which resulted from the cross pollination of male parent *Tillandsia laxissima* (unnamed and unpatented) and a female parent breeding line of *Tillandsia cyanea* (unnamed and unpatented), owned and previously bred by the inventor, which exhibits a branched inflorescence. Progeny of said cross were observed for desired commercial characteristics and, in September of 2010, 'Duraant' was observed in bloom and selected for its high degree of branching of the inflorescence.

Asexual Reproduction: 'Duraant' was first asexually propagated by tissue culture in February of 2009 at a laboratory in Alajuela, Costa Rica under the control of the inventor. The distinctive characteristics of the inventive 'Duraant' variety are stable from generation to generation; clones of the variety produced by asexual reproduction maintain the distinguishing characteristics of the original plant.

SUMMARY OF THE INVENTION

The following characteristics have been repeatedly observed and represent the distinguishing characteristics of the new *Tillandsia* cultivar 'Duraant'. These traits in combination distinguish 'Duraant' as a new and distinct cultivar.

1. *Tillandsia* 'Duraant' exhibits a high degree of inflorescence branching.

2. *Tillandsia* 'Duraant' exhibits striking pink bracts.
3. *Tillandsia* 'Duraant' exhibits dark green foliage.

Colors in the photographs differ slightly from the color values cited in the detailed description, which accurately describes the colors of 'Duraant'.

Figure 1:
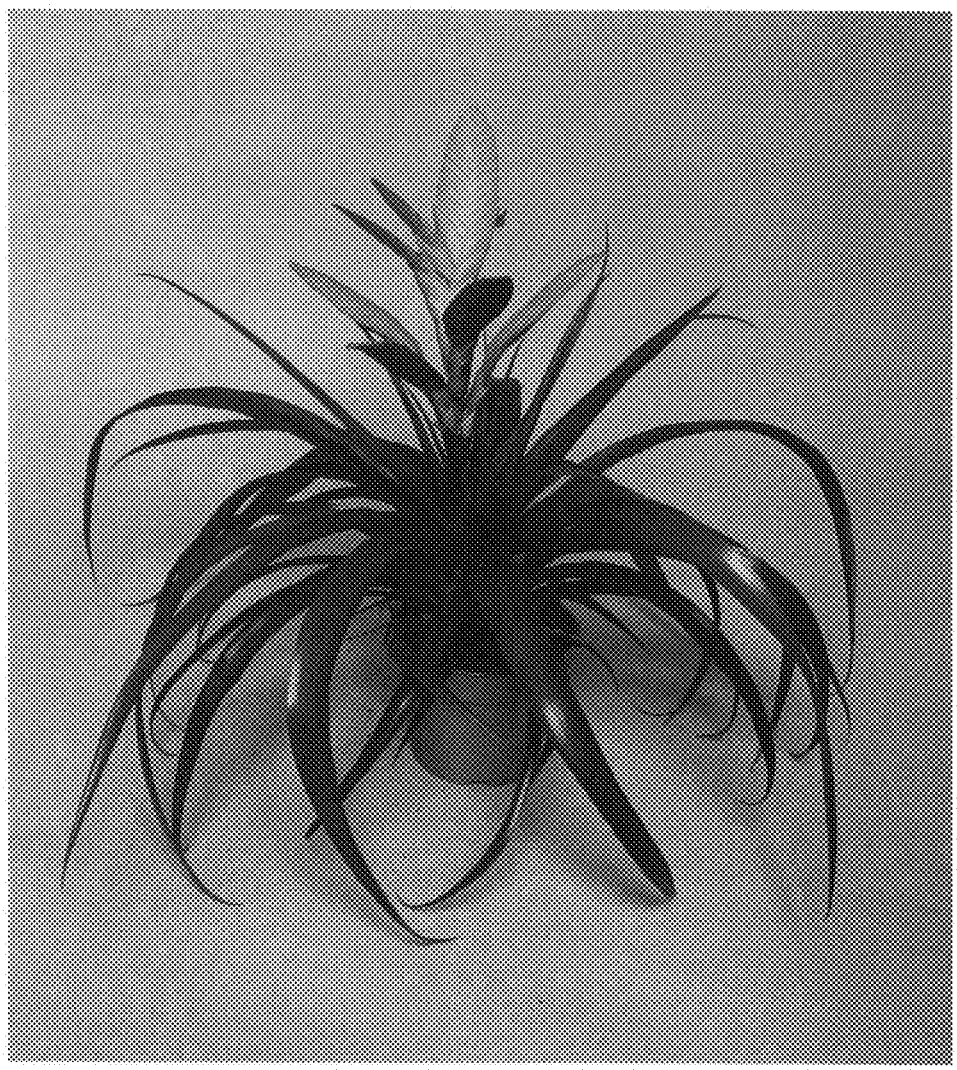
FIG. 1 shows, as nearly true as it is reasonably possible to make the same in color illustrations of this type, the typical foliage, inflorescence, and growth characteristics of the new cultivar, 'Duraant'. The plant shown is approximately 14 months old from a rooted cutting, potted into a 12 cm nursery pot, grown in a climate-controlled greenhouse in Evergem, Belgium.
Figure 2:
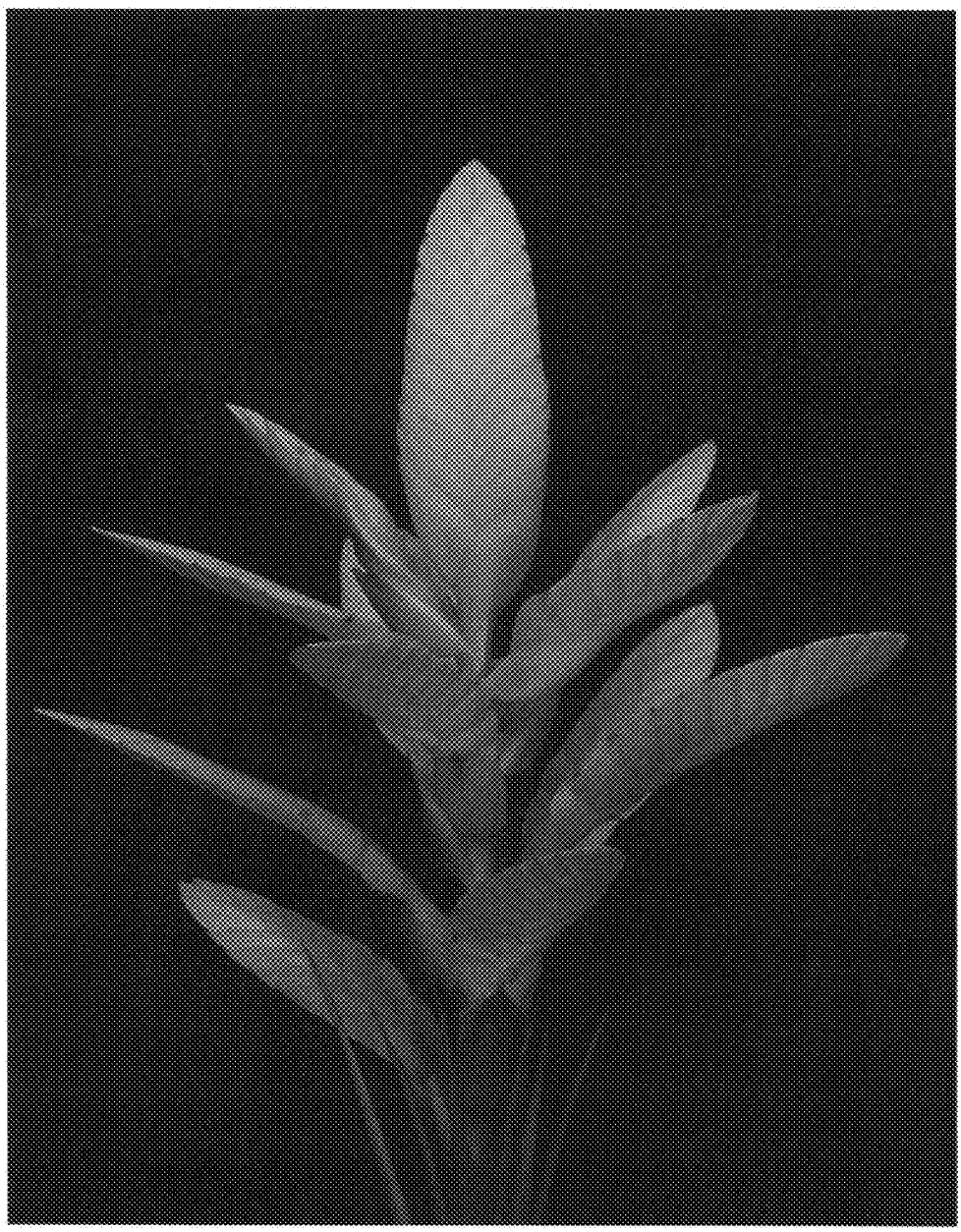

FIG. 2 shows the prominent pink coloration of the bracts of 'Duraant' and also the high degree of branching of the inflorescence.

BOTANICAL DESCRIPTION OF THE PLANT

The following is a detailed botanical description of a new and distinct variety of *Tillandsia* hybrid known as 'Duraant', based upon observations of plants, approximately 14 months old from a rooted cutting, potted into a 12 cm nursery pot, grown in a climate-controlled greenhouse in Evergem, Belgium. Temperatures ranged from 20 to 28 degrees Celsius during the day and 18 to 22 degrees Celsius at night. No artificial light, photoperiodic treatments or chemical treatments were given to the plants. Measurements and numerical values represent averages of typical plant types. Observation data was recorded in November of 2014.

Those skilled in the art will appreciate that certain characteristics will vary with older or, conversely, with younger plants. 'Duraant' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, 2007 edition.

A botanical description of 'Duraant' and comparisons with other varieties of *Tillandsia* hybrid are provided below.

Technical Description of the Variety.

Plant description:

*Vigor.*—Moderate.
*Growth rate.*—Moderate.
*Growth habit.*—Broad spreading from a basal rosette.
*Plant shape.*—Low and spreading with inflorescences growing from the center of the basal rosette.
*Height.*—Average 26.8 cm in height.
*Width.*—Average 54.6 cm in width.
*Hardiness.*—USDA Zone 10.
*Container size.*—11 cm circular pot.
*Propagation.*—Tissue culture.
*Time to initiate roots.*—Approximately 15 days to initiate roots at 20° Centigrade.
*Time to produce a rooted cutting or liner in summer.*—Approximately 180 days to produce a rooted cutting or liner at 22° Centigrade.
*Time to produce a rooted cutting or liner in winter.*—Approximately 7 months to produce a rooted cutting or liner at 25° Centigrade.
*Disease resistance.*—Plants of the new *Tillandsia* are resistant to root diseases.
*Pest resistance.*—Plants of the new *Tillandsia* have not been observed for pest resistance.

Root system: Fine and fibrous.

Foliage:

*Texture.*—Glabrous, moderately glossy.
*Leaf arrangement.*—Rosulate, placed in a basal rosette.
*Quantity of leaves per plant.*—39.
*Leaf shape.*—Linear, arching downward; blade involute.
*Leaf apex.*—Long and narrow acute.
*Leaf base.*—Sheathing.
*Leaf length.*—Average 36.8 cm in length.
*Leaf width.*—Average 2.2 cm in width.
*Pubescence.*—Absent.
*Leaf margin.*—Entire.
*Vein pattern.*—Parallel.
*Young leaf color* (*upper surface*).—Between 143A and 146A but darker, tipped and slightly blotched 183A to 183B.
*Young leaf color* (*lower surface*).—146A, heavily blotched and tipped in between 183A and 200B.
*Mature leaf color* (*upper surface*).—Between 143A and 146A but darker, tipped 200B, base 146B.
*Mature leaf color* (*lower surface*).—147B, tipped 200B, base 148B and 148C, moderately blotched 183B.
*Vein color* (*lower surface*).—As leaf surface: 147A.
*Vein color* (*upper surface*).—As leaf surface: between 143A and 146A but darker.
*Durability of foliage to stress.*—High.

Flower:

*Flowering arrangement.*—Terminal compound panicle.
*Inflorescence type.*—Panicle.
*Inflorescence dimensions.*—Average width 7.5 cm. and 17.0 cm in height (measured from lowest branching of inflorescence).
*Flowering habit.*—Continuous.
*Flower form.*—Single.
*Quantity of flowers per inflorescence.*—Average 64.
*Quantity of flower stems per plant.*—Average 1.
*Quantity of flowers and buds per plant.*—Average 64.
*Flowering season.*—Winter.
*Rate of flower opening.*—5% of the flowers are open at any stage.
*Fragrance.*—Moderately faint.
*Self-cleaning or persistent.*—Persistent.
*Flower bud length.*—1.7 cm in length.
*Flower bud diameter.*—0.25 cm in diameter.
*Flower bud shape.*—Linear, bud enclosed by a colorful bract.
*Bud color.*—145D; base 157D.
*Rate of bud opening.*—10 days.
*Flower aspect.*—Upward to slightly outward.
*Flower shape.*—Salverform.
*Flower width.*—1.8 cm.
*Flower height.*—2.0 cm.
*Flower longevity.*—Over 14 days.
*Petal appearance.*—Matte, glabrous.
*Petal texture.*—Glabrous.
*Petal arrangement.*—Rotate.
*Number of petals.*—Three in number.
*Petals fused or unfused.*—Unfused.
*Petal shape.*—Spathulate.
*Petal margin.*—Entire.
*Petal apex.*—Broad acute.
*Petal dimensions.*—2.2 cm in length and 1.1 cm in width.
*Petal color when opening* (*upper side*).—N88A.
*Petal color when opening* (*under side*).—N88B.
*Petal color when fully opened* (*upper side*).—N88D.
*Petal color when fully opened* (*under side*).—N88C.
*Petal color fading.*—Not fading.
*Sepals.*—Sepal appearance — Glossy and smooth. Sepal arrangement — Paired, placed at both sides of the corolla. Number of sepals — Two in number. Sepal shape — Lanceolate, involute. Sepal margin — Entire. Sepal tip — Acute. Sepal base — Cuneate. Sepal length — Average 2.6 cm. Sepal width — Average 0.4 cm. Sepal color, immature, upper surface — 145C, margins 63B. Sepal color, immature, under surface — 145C, margins 63B. Sepal color, mature, upper surface — 145C, margins 63C. Sepal color, mature, under surface — 145C, margins 63C.
*Calyx.*—Calyx shape — Tubular. Calyx length — Average 2.6 cm in length. Calyx width — Average 0.7 cm in diameter.
*Peduncle.*—Peduncle dimensions — Average 18.5 cm in length and 0.8 cm in diameter. Peduncle angle — 0° (vertical). Peduncle color — 145A and 145B. Peduncle strength — Strong.

Bracts:

*Bract quantity.*—1 per individual flower.
*Bract shape.*—Broad ovate, folded lengthways.
*Bract dimensions.*—Average 3.9 cm in length, 0.6 cm in width.
*Bract tip.*—Broad acute.
*Bract margin.*—Entire.
*Bract base.*—Sheathing.
*Bract color upper side.*—73A.
*Bract color under side.*—65C.

Reproductive organs:

*Stamen quantity.*—Average 6.
*Anther shape.*—Linear.
*Anther size.*—0.4 cm.
*Anther filament size.*—1.4 cm.

*Anther color.*—11A.
*Amount of pollen.*—High.
*Pollen color.*—11A.
*Pistil number.*—One in number.
*Pistil length.*—Average 0.5 cm.
*Stigma shape.*—Club-shaped.
*Stigma color.*—150D.
*Style length.*—0.3 cm.
*Style color.*—150D.
*Ovary color.*—155C.

Seed and fruit: Seed production has not been observed.

Comparisons With Parent Plants

Plants of the new cultivar 'Duraant' are similar to female parent in many horticultural characteristics. However, the inflorescence of 'Duraant' is highly branched with a long peduncle, whereas the inflorescence of the female parent is branched but has no discernable peduncle. Furthermore, the inflorescence of 'Duraant' is taller than that of the female parent. The leaf of 'Duraant' is wider than that of the female plant.

The inflorescence of 'Duraant' is shorter than that of the male parent. The inflorescence of the male parent has a different shape. That is, 'Duraant' exhibits a higher number of bracts, each bract having a narrower width. Also, the foliage of 'Duraant' is narrower than that of the male parent.

Comparisons With Other Commercial *Tillandsia*

Plants of the new cultivar 'Duraant' are comparable to the commercial variety *Tillandsia cyanea* 'Josee' (U.S. Plant Pat. No. 20,014) in that both varieties exhibit branched inflorescence. However, 'Duraant' exhibits larger inflorescence when compared to those of 'Josee', and the conspicuous bracts of 'Duraant' are longer and narrower than those of 'Josee'. Also, the peduncles of 'Duraant' are more curved by comparison to the peduncles of 'Josee'. Furthermore, the foliage of 'Duraant' is wider than the foliage of 'Josee'.

Plants of the new cultivar 'Duraant' are also comparable to the commercial variety *Tillandsia cyanea* 'Anita' (unpatented) in many horticultural characteristics. However, 'Anita' does not possess branched inflorescence.

That which is claimed is:

1. A new and distinct variety of *Tillandsia* hybrid plant named 'Duraant', substantially as described and illustrated herein.

* * * * *